US007148251B2

(12) United States Patent
Shayman

(10) Patent No.: US 7,148,251 B2
(45) Date of Patent: Dec. 12, 2006

(54) AMINO CERAMIDE-LIKE COMPOUNDS AND THERAPEUTIC METHODS OF USE

(75) Inventor: James A. Shayman, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/044,869

(22) Filed: Jan. 10, 2002

(65) Prior Publication Data

US 2002/0156107 A1    Oct. 24, 2002

Related U.S. Application Data

(60) Provisional application No. 60/262,196, filed on Jan. 17, 2001, provisional application No. 60/260,948, filed on Jan. 10, 2001.

(51) Int. Cl.
*A61K 31/396* (2006.01)
*A61K 31/397* (2006.01)
*A61K 31/40* (2006.01)
*A61K 31/4453* (2006.01)
*A61K 31/5375* (2006.01)
*C07D 207/04* (2006.01)
*C07D 211/06* (2006.01)
*C07D 265/30* (2006.01)
*C07D 205/04* (2006.01)
*C07D 203/06* (2006.01)

(52) U.S. Cl. .................. 514/428; 514/210.1; 514/315; 514/237.8; 514/408; 514/428; 544/162; 546/233; 548/568; 548/579; 548/950; 548/954

(58) Field of Classification Search ................ 514/428, 514/315, 231.2, 210.1, 408; 548/568, 579; 548/237.8; 546/247, 233; 544/106, 162; 540/950, 954
See application file for complete search history.

(56) References Cited

U.S. PATENT DOCUMENTS

| | | | | |
|---|---|---|---|---|
| 5,916,911 A | * | 6/1999 | Shayman et al. | 514/428 |
| 5,945,442 A | | 8/1999 | Shayman et al. | |
| 5,952,370 A | | 9/1999 | Shayman et al. | |
| 6,030,995 A | * | 2/2000 | Shayman et al. | 514/428 |
| 6,040,332 A | | 3/2000 | Shayman et al. | |
| 6,051,598 A | | 4/2000 | Shayman et al. | |

FOREIGN PATENT DOCUMENTS

JP        10-324671        12/1998

JP    10324671 A2    12/1998
WO    WO 9710817    3/1997

OTHER PUBLICATIONS

CAPLUS listing of Accession No. 1985:221199, Keith McCullagh et al, "Carboxyalkyl peptide derivatives."*
Abe, A. et al., *J. Biochem.*, 111:191-196 (1992).
Alon, R. et al., *J. Immunol.*, 154:5356-5366 (1995).
Bielawska, A. et al., *FEBS Letters.*, 307:211-214 (1992).
Blobe, G.C. et al., *Cancer Metastasis Rev.*, 13:411-431 (1994).
Brenkert, A. et al., *Brain Res.*, 36:183-193 (1972).
Felding-Habermann, B. et al., *Biochemistry*, 29:6314-6322 (1990).
Hakomori, S., *Cancer Cells*, 3:461-470 (1991).
Hospattankar, A.V. et al., *Lipids*, 17:538-543 (1982).
Inokuchi, J. et al., *Cancer Leters*, 38:23-30 (1987).
Inokuchi, J. et al., *Cancer Res.*, 50:6731-6737 (1990).
Inokuchi, J. et al., *J. Lipid Res.*, 28:565-571 (1987).
Jaffrézou, J. et al., *Biochim. Biophys. Acta*, 1266:1-8 (1995).
Radin, N.S. et al., *Advances in Lipid Research; Sphingolipids in Signaling, Part B.*, R.M. Bell et al., Ed. (Academic Press, San Diego), 28:183-213 (1993).
Radin, N.S. et al., *NeuroProtocols, A Companion to Methods in Neurosciences*, S.K. Fisher et al., Ed., (Academic Press, San Diego), 3:145-155 (1993).
Rosenwald, A.G. et al., *J. Lipid Res.*, 35:1232-1240 (1994).
Shayman, J.A. et al., *J. Biol. Chem.*, 266:22968-22974 (1991).
Svensson, M. et al., *Infect. and Immun.*, 62:4404-4410 (1994).
Zador, I.Z. et al., *J. Clin. Invest.*, 91:797-803 (1993).
Ziche, M. et al., *Lab. Invest.*, 67:711-715 (1992).
Lee, L., et al., "Improved Inhibitors of Glucosylceramide Synthase," *Journal of Biological Chemistry*, 274(21):14662-14669 (1999).
Gatt, S., et al., "Assay of Enzymes of Lipid Metabolism with Colored and Fluorescent Derivatives of Natural Lipids," *Methods in Enzymology.*, 72:351-375 (1981).
Inokuchi, et al., "Amino Alcohol Esters as Ceramide Analogs and Pharmaceuticals Containing Them for Treatment of Nerve Diseases," Abstract of Caplus Accession No. 1998:786189, JP 10324671 (1998).

* cited by examiner

Primary Examiner—Joseph K. McKane
Assistant Examiner—Janet L. Coppins
(74) Attorney, Agent, or Firm—Hamilton, Brook, Smith & Reynolds, P.C.

(57) ABSTRACT

Novel prodrugs of amino ceramide-like compounds are provided which inhibit glucosyl ceramide (GlcCer) formation by inhibiting the enzyme GlcCer synthase, thereby lowering the level of glycosphingolipids. The compounds of the present invention have improved GlcCer synthase inhibition activity and are therefore highly useful in therapeutic methods for treating various conditions and diseases associated with altered glycosphingolipid levels.

14 Claims, 3 Drawing Sheets

I. w/o cytosol

II. w/o cytosol

I. w/ cytosol

II. w/ cytosol

US 7,148,251 B2

AMINO CERAMIDE-LIKE COMPOUNDS AND THERAPEUTIC METHODS OF USE

RELATED APPLICATIONS

This application claims priority to U.S. Provisional Application Ser. No. 60/260,948, filed Jan. 10, 2001 and U.S. Provisional Application Ser. No. 60/262,196, filed Jan. 17 2001.

SPONSORSHIP

Work on this invention was sponsored in part by National Institutes of Health Grant R01 DK55823. The Government may have certain rights in the invention.

FIELD OF THE INVENTION

The present invention relates generally to ceramide-like compounds and, more particularly, to prodrugs of ceramide-like compounds that inhibit glucosylceramide formation.

BACKGROUND OF THE INVENTION

Hundreds of glycosphingolipids (GSLs) are derived from glucosylceramide (GlcCer), which is enzymatically formed from ceramide and UDP-glucose. The enzyme involved in GlcCer formation is UDP-glucose:N-acylsphingosine glucosyltransferase (GlcCer synthase). The rate of GlcCer formation under physiological conditions may depend on the tissue level of UDP-glucose, which in turn depends on the level of glucose in a particular tissue (Zador, I. Z. et al., "A Role for Glycosphingolipid Accumulation in the Renal Hypertrophy of Streptozotocin-Induced Diabetes Mellitus," *J. Clin. Invest* 91:797–803 (1993)). In vitro assays based on endogenous ceramide yield lower synthetic rates than mixtures containing added ceramide, suggesting that tissue levels of ceramide are also normally rate-limiting (Brenkert, A. et al., "Synthesis of Galactosyl Ceramide and Glucosyl Ceramide by Rat Brain: Assay Procedures and Changes with Age," *Brain Res.* 36:183–193 (1972)).

It has been found that the level of GSLs controls a variety of cell functions, such as growth, differentiation, adhesion between cells or between cells and matrix proteins, binding of microorganisms and viruses to cells, and metastasis of tumor cells. In addition, the GlcCer precursor, ceramide, may cause differentiation or inhibition of cell growth (Bielawska, A. et al., "Modulation of Cell Growth and Differentiation by Ceramide," *FEBS Letters* 307:211–214 (1992)) and be involved in the functioning of vitamin $D_3$, tumor necrosis factor-$\alpha$, interleukins, and apoptosis (programmed cell death). The sphingols (sphingoid bases), precursors of ceramide, and products of ceramide catabolism, have also been shown to influence many cell systems, possibly by inhibiting protein kinase C (PKC).

It is likely that all the GSLs undergo catabolic hydrolysis, so any blockage in the GlcCer synthase should ultimately lead to depletion of the GSLs and profound changes in the functioning of a cell or organism. An inhibitor of GlcCer synthase, PDMP (1R-phenyl-2R-decanoylamino-3-morpholino-1-propanol), previously identified as the D-threo isomer (Inokuchi, J. et al., "Preparation of the Active Isomer of 1-Phenyl-2-Decanoylamino-3-Morpholino1-Propanol, Inhibitor of Glucocerebroside Synthetase," *J. Lipid Res.* 28:565–571 (1987)), has been found to produce a variety of chemical and physiological changes in cells and animals (Radin, N. S. et al., "Use of 1-Phenyl-2-Decanoylamino-3-Morpholino-1-Propanol (PDMP), an Inhibitor of Glucosylceramide Synthesis," In *NeuroProtocols, A Companion to Methods in Neurosciences*, S. K. Fisher et al., Ed., (Academic Press, San Diego) 3:145–155 (1993) and Radin, N. S. et al., "Metabolic Effects of Inhibiting Glucosylceramide Synthesis with PDMP and Other Substances," In *Advances in Lipid Research; Sphingolipids in Signaling, Part B.*, R. M. Bell et al., Ed. (Academic Press, San Diego) 28:183–213 (1993)). Particularly interesting is the compound's ability to cure mice of cancer induced by Ehrlich ascites carcinoma cells (Inokuchi, J. et al., "Antitumor Activity in Mice of an Inhibitor of Glycosphingolipid Biosynthesis," *Cancer Lett.* 38:23–30 (1987)), to produce accumulation of sphingosine and N,N-dimethylsphingosine (Felding-Habermann, B. et al., "A Ceramide Analog Inhibits T Cell Proliferative Response Through Inhibition of Glycosphingolipid Synthesis and Enhancement of N,N-Dimethylsphingosine Synthesis," *Biochemistry* 29:6314–6322 (1990)), and to slow cell growth (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)). Compounds with longer chain fatty acyl groups have been found to be substantially more effective (Abe, A. et al., "Improved Inhibitors of Glucosylceramide Synthesis," *J. Biochem.* 111: 191–196 (1992)).

The importance of GSL metabolism is underscored by the seriousness of disorders resulting from defects in GSL metabolizing enzymes. For example, Tay-Sachs, Gaucher's, and Fabry's diseases, resulting from enzymatic defects in the GSL degradative pathway and the accumulation of GSL in the patient, all have severe clinical manifestations. Another example of the importance of GSL function is seen in a mechanism by which blood cells, whose surfaces contain selecting, can, under certain conditions, bind to GSLs in the blood vessel walls and produce acute, life-threatening inflammation (Alon, R. et al., "Glycolipid Ligands for Selectins Support Leukocyte Tethering & Rolling Under Physiologic Flow Conditions." *J. Immunol.*, 154: 5356–5366 (1995)).

At present there is only one treatment available for patients with Gaucher disease, wherein the normal enzyme which has been isolated from normal human tissues or cultured cells is administered to the patient. As with any drug isolated from human material, great care is needed to prevent contamination with a virus or other dangerous substances. Treatment for an individual patient is extremely expensive, costing hundreds of thousands, or even millions of dollars, over a patient's lifetime. It would thus be desirable to provide a treatment which includes administration of a compound that is readily available and/or producible from common materials by simple reactions.

Possibly of even greater clinical relevance is the role of glucolipids in cancer. For example, it has been found that certain GSLs occur only in tumors; certain GSLs occur at abnormally high concentrations in tumors; certain GSLs, added to tumor cells in culture media, exert marked stimulatory or inhibitory actions on tumor growth; antibodies to certain GSLs inhibit the growth of tumors; the GSLs that are shed by tumors into the surrounding extracellular fluid inhibit the body's normal immunodefense system; the composition of a tumor's GSLs changes as the tumors become increasingly malignant; and, in certain kinds of cancer, the level of a GSL circulating in the blood gives useful information regarding the patient's response to treatment. Because of the significant impact GSLs have on several biochemical processes, there remains a need for compounds having improved GlcCer synthase inhibition activity.

It would thus be desirable to provide compounds which inhibit GlcCer synthase activity. It would also be desirable to provide compounds which inhibit GlcCer synthase activity, thereby lowering the level of GSLs and increasing GSL precursor levels, e.g. increasing the levels of ceramide and sphingols. It would further be desirable to provide compounds which inhibit GlcCer synthase activity and lower the level of GSLs without also increasing ceramide levels. It would also be desirable to provide compounds and therapeutic methods to treat conditions and diseases associated with altered GSL levels and/or GSL precursor levels. It would be further desirable to provide such compounds in the form of prodrugs that are then transformed into the active compounds within a cell.

SUMMARY OF THE INVENTION

Novel compounds are provided which inhibit GlcCer formation by inhibiting the enzyme GlcCer synthase, thereby lowering the level of GSLs. The compounds of the present invention are in the form of prodrugs. As prodrugs, they are in an inactive form unitl they are introduced into a cell or organism, where they are then converted to an active form. Active compounds are also provided that are more hydrophobic to aid in transport across cell membranes thus increasing the concentration of the compounds in the target cells. The active forms of the compounds of the present invention have improved GlcCer synthase inhibition activity and are therefore highly useful in therapeutic methods for treating various conditions and diseases associated with altered GSL levels, as well as GSL precursor levels. For example, the compounds of the present invention may be useful in methods involving cancer growth and metastasis, the growth of normal tissues, the ability of pathogenic microorganisms to bind to normal cells, the binding between similar cells, the binding of toxins to human cells, and the ability of cancer cells to block the normal process of immunological cytotoxic attack.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Novel compounds in the form of prodrugs are provided which inhibit GlcCer formation by inhibiting the enzyme GlcCer synthase, thereby lowering the level of GSLs. The compounds of the present invention are converted to their active form once they have been taken up by a cell. The compounds of the present invention have improved GlcCer synthase inhibitory activity and are therefore highly useful in therapeutic methods for treating various conditions and diseases associated with altered GSL levels. The prodrugs have improved pharmacokinetic properties, including improved transport into the cells. Once the prodrug enters the target cell or organism, it is converted into the active form by metabolic processes.

The compounds of the present invention generally have the following formula:

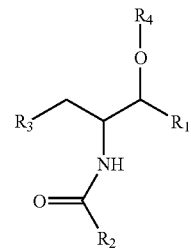

wherein $R_1$ is a phenyl group, preferably a substituted phenyl group such as p-methoxy, hydroxy, dioxane substitutions such as methylenedioxy, ethylenedioxy, and trimethylenedioxy, cyclohexyl or other acyclic group, t-butyl or other branched aliphatic group, or a long alkyl or alkenyl chain, preferably 7 to 15 carbons long with a double bond next to the kernel of the structure. The aliphatic chain can have a hydroxyl group near the two asymmetric centers, corresponding to phytosphingosine.

$R_2$ is an alkyl residue of a fatty acid, 10 to 18 carbons long. The fatty acid can be saturated or unsaturated, or possess a small substitution at the C-2 position (e.g., a hydroxyl group).

$R_3$ is a tertiary amine, preferably a cyclic amine such as pyrrolidine, azetidine, morpholine or piperidine, in which the nitrogen atom is attached to the kernel (i.e., a tertiary amine).

$R_4$ is any group that is selectively hydrolyzed in a target cell, preferrably an acetyl, $-CO(CH_2)_nCH_3$ wherein n is at least 1,

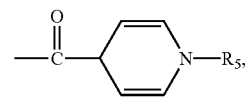

wherein $R_5$ is an alkyl group.

The compounds of the present invention are converted in the cell to the active, inhibitory forms of the compounds having the general formula:

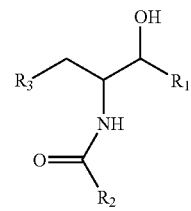

wherein $R_1$, $R_2$ and $R_3$ are defined above for the prodrug compounds.

All four structural isomers of the compounds are contemplated within the present invention and may be used either singly or in combination (i.e., DL-threo or DL-erythro).

In one embodiment, the compounds of the present invention include the prodrugs of the GlcCer Synthase inhibitors disclosed in U.S. Pat. No. 6,030,995, hereby incorporated by reference. The prodrug compounds comprise a hydrolyzable group covalently bonded to the oxygen of the hydroxyl of the 1-propanol backbone. Preferred compounds of the present invention are the prodrugs of D-t-3',4',-ethylenedioxy-1-phenyl-2-palmitoylamino-3-pyrrolidino-1-propanol, also referred to herein as D-t-3',4',-ethylenedioxy-P4 (or D-t-EtDO-P4 in the figures), and D-t-4'-hydroxy-1-phenyl-2-palmitoylamino-3-pyrrolidino-1-propanol, also referred to herein as D-t-4'-hydroxy-P4.

Figure 3:
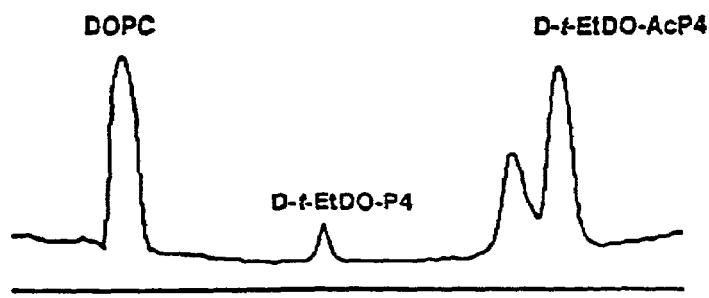
FIG. 3 is an HPLC trace showing the conversion of the prodrug into the active compound in the presence of liver cytosol.
Figure 3:
Figure 3:
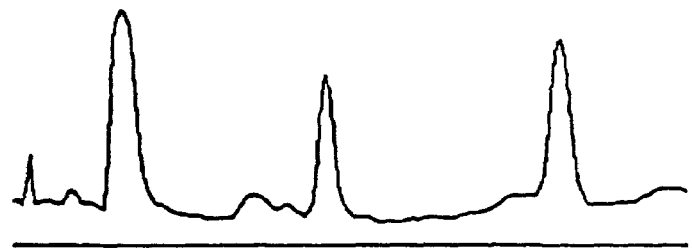
Figure 3:
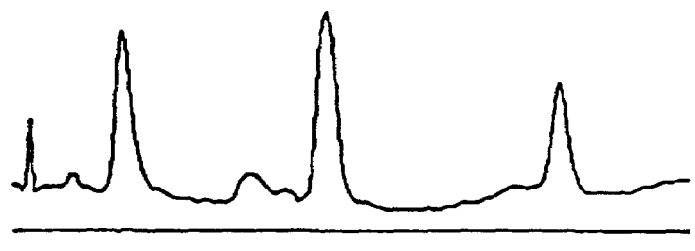

In another embodiment of the present invention the prodrugs of the present invention comprise a covalently attached hydrolyzable group ($R_4$) to the hydroxyl of the 1-propanol backbone that is selectively hydrolyzed within the cell, preferably enzymatically. The chemical moeity can be any group that is selectively hydrolyzed to produce an active compound with a unmodified hydroxyl in the cell. As a non-limiting example, FIG. 3 shows the selective conversion of acetyl-modified D-t-3',4'-ethylenedioxy-P4 in the presence of cytosol. In the absence of cytosol, the prodrug is not converted to the active compound in an aqueous solution.

In a preferred embodiment, the group is attached to the active compound through an ester bond. The chemical group preferably is an acetyl, —$CO(CH_2)_nCH_3$ wherein n is at least 1 or

Figure 1:
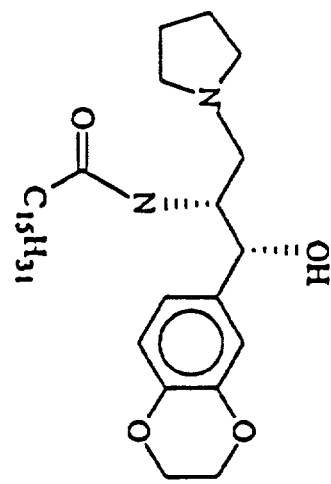
FIG. 1 is a schematic showing the structure of carbon-3 substituted homologues of ethylenedioxy-P4.
Figure 1:
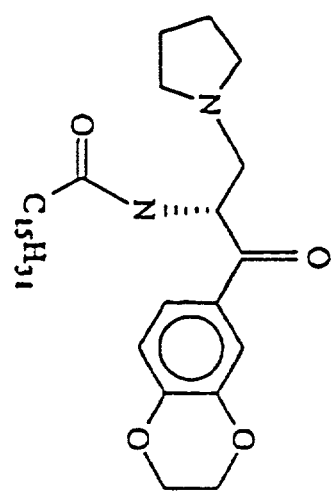
Figure 1:
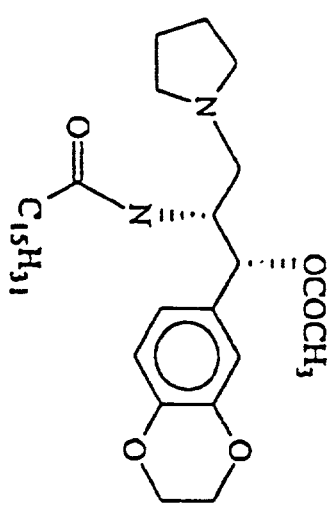
Figure 2:
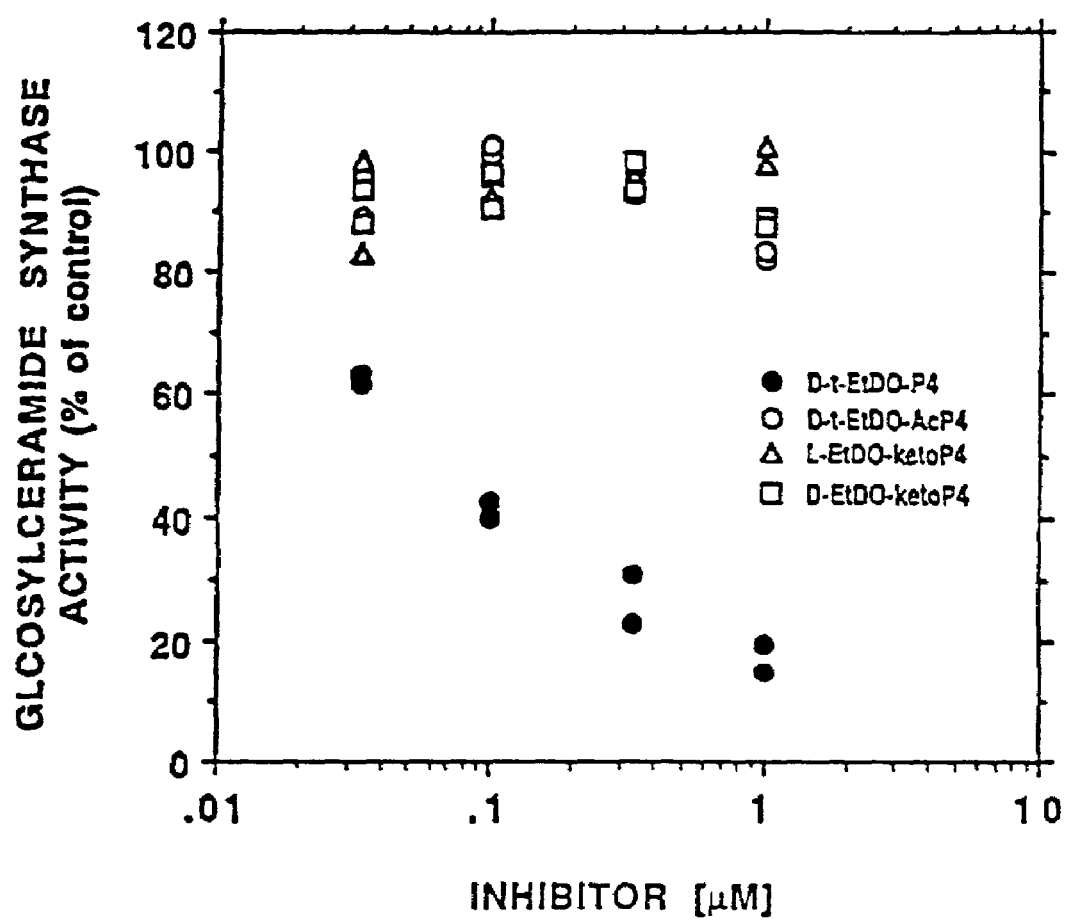
FIG. 2 is a graph showing the inhibition of glucosylceramide synthase by D-t-ethylenedioxy-P4 and prodrugs of ethylenedioxy-P4.

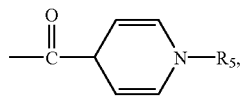

wherein $R_5$ is an alkyl group. The modified prodrugs are inactive as inhibiters of GlcCer Synthase (open symbols, FIG. 2). However, cleavage of the chemical moeity to form an unmodified hydroxyl produces a potent inhibitor (FIG. 2).

In another embodiment, the compounds of the present invention are prodrugs in which $R_1$ is 4'-hydroxy-phenyl and the hydrolyzable group ($R_6$) is covalently bound to the 4'-hydroxy. These compounds have the general formula:

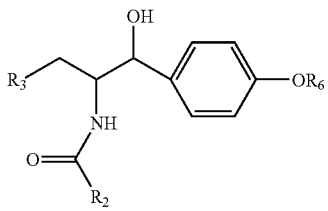

wherein $R_2$ is an alkyl residue of a fatty acid, 10 to 18 carbons long. The fatty acid can be saturated or unsaturated, or possess a small substitution at the C-2 position (e.g., a hydroxyl group).

$R_3$ is a tertiary amine, preferably a cyclic amine such as pyrrolidine, azetidine, morpholine or piperidine, in which the, nitrogen atom is attached to the kernel (i.e., a tertiary amine).

$R_6$ is any group that is selectively hydrolyzed in a target cell, preferably an acetyl, —$CO(CH_2)_nCH_3$ wherein n is at least 1,

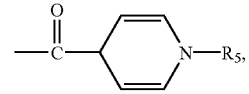

wherein $R_5$ is an alkyl group.

Hydrolysis of the group covalently attached to the 4'-hydroxyl within the cell produces an active compound having a free 4'-hydroxyl. A preferred compound is the prodrug of D-t-4'-hydroxy-P4.

In yet another embodiment, the compounds of the present invention are prodrugs in which $R_1$ is 4'-hydroxy-phenyl and where hydrolyzable groups are covalently bound to both the hydroxyl of the 1-propanol backbone ($R_4$) and the 4'-hydroxy of the phenyl ($R_6$). The general structure of these compounds is:

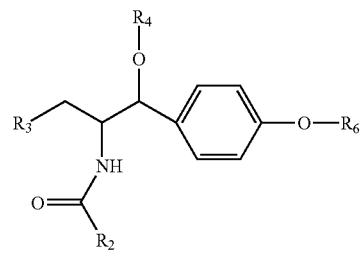

wherein $R_2$ is an alkyl residue of a fatty acid, 10 to 18 carbons long. The fatty acid can be saturated or unsaturated, or possess a small substitution at the C-2 position (e.g., a hydroxyl group).

$R_3$ is a tertiary amine, preferably a cyclic amine such as pyrrolidine, azetidine, morpholine or piperidine, in which the nitrogen atom is attached to the kernel (i.e., a tertiary amine).

$R_4$ and $R_6$ are any group that is selectively hydrolyzed in a target cell, preferably an acetyl, —$CO(CH_2)_nCH_3$ wherein n is at least 1,

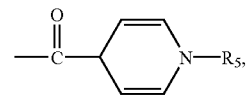

wherein $R_5$ is an alkyl group.

The pharmacokinetic properties of an active compound can be enhanced by making the molecule more lipophilic. One advantage is increasing the permeability across the cell membrane, resulting in higher intracellular concentrations of the active compound. In one embodiment, an alkyl group is covalently bound to the compound of the present invention. These compounds may have the general formula:

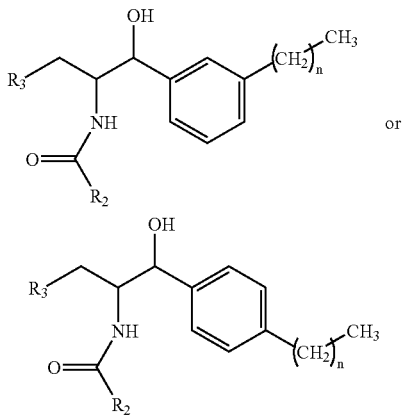

wherein n is an integer from about 1 to about 19;

$R_2$ is an alkyl residue of a fatty acid, 10 to 18 carbons long. The fatty acid can be saturated or unsaturated, or possess a small substitution at the C-2 position (e.g., a hydroxyl group).

$R_3$ is a tertiary amine, preferably a cyclic amine such as pyrrolidine, azetidine, morpholine or piperidine, in which the nitrogen atom is attached to the kernel (i.e., a tertiary amine).

The alkyl chain attached to the phenyl group makes the active compound more lipophilic, allowing a higher concentration to get into the target cells. Preferably the alkyl chain in unsaturated. The presence of the alkyl chain results in an active compound that resembles the naturally occuring substrate of GlcCer Synthase, which comprises a sphingosine.

The compounds of the present invention are easily synthesized by methods well known in the art. For example, the compounds of the present invention can be synthesized by esterification of the hydroxy (or alcohol) with the appropriate anhydride.

In one embodiment of the present invention, methods of treating patients suffering from inborn genetic errors in the metabolism of GlcCer and its normal anabolic products (lactosylceramide and the more complex GSLs) with the prodrugs are provided. The presently known disorders in this category include Gaucher, Fabry, Tay-Sachs, Sandhoff, and GM1 gangliosidosis. The genetic errors lie in the patient's inability to synthesize a hydrolytic enzyme having normal efficiency. Their inefficient hydrolase allows the GSL to gradually accumulate to a toxic degree, debilitating or killing the victim. The compounds of the present invention slow the formation of GSLs, thus allowing the defective hydrolase to gradually "catch up" and restore the concentrations of GSLs to their normal levels and thus the compounds may be administered to treat such patients.

With respect to Gaucher disease, it has been calculated that much of the patient's accumulated GlcCer in liver and spleen arises from the blood cells, which are ultimately destroyed in these organs after they have reached the end of their life span. The actual fraction, lipid derived from blood cells versus lipid formed in the liver and spleen cells, is actually quite uncertain, but the external source must be important. Therefore it is necessary for the compounds of the present invention to deplete the blood cells as they are formed or (in the case of white blood cells) while they still circulate in the blood. Judging from toxicity tests, the white cells continue to function adequately despite their loss of GSLs. Although the toxicity studies were not of a long enough duration to produce many new red cells with low GSL content, it is possible that circulating red cells also undergo turnover (continual loss plus replacement) of GSLs.

In an alternative embodiment of the present invention, for the treatment of disorders involving cell growth and division, high dosages of the compounds of the present invention are administered but only for a relatively short time. These disorders include cancer, collagen vascular diseases, atherosclerosis, and the renal hypertrophy of diabetic patients. Accumulation or changes in the cellular levels of GSLs have been implicated in these disorders and blocking GSL biosynthesis would allow the normal restorative mechanisms of the body to resolve the imbalance.

With atherosclerosis, it has been shown that arterial epithelial cells grow faster in the presence of a GlcCer product (lactosylceramide). Oxidized serum lipoprotein, a material that normally circulates in the blood, stimulates the formation of plaques and lactosylceramide in the inner lining of blood vessels. Treatment with the compounds of the present invention would inhibit this mitogenic effect.

In an additional embodiment of the present invention, patients suffering from infections may be treated with the compounds of the present invention. Many types of pathogenic bacteria have to bind to specific GSLs before they can induce their toxic effects. As shown in Svensson, M. et al., "Epithelial Glucosphingolipid Expression as a Determinant of Bacterial Adherence and Cytokine Production," *Infect and Immun.* 62:4404–4410 (1994), expressly incorporated by reference, PDMP treatment reduces the adherence of *E. coli* to mammalian cells. Several viruses, such as influenza type A, also must bind to a GSL. Several bacterial toxins, such as the verotoxins, cannot themselves act without first binding to a GSL. Thus, by lowering the level of GSLs, the degree of infection may be ameliorated. In addition, when a patient is already infected to a recognizable, diagnosable degree, the compounds of the present invention may slow the further development of the infection by eliminating the binding sites that remain free.

It has been shown that tumors produce substances, namely gangliosides, a family of GSLs, that prevent the host i.e., patient, from generating antibodies against the tumor. By blocking the tumor's ability to secrete these substances, antibodies against the tumor can be produced. Thus, by administering the GlcCer synthase inhibitors of the present invention to the patient, the tumors will become depleted of their GSLs and the body's normal immunological defenses will come into action and destroy the tumor. This technique was described in Inokuchi, J. et al., "Antitumor Activity in Mice of an Inhibitor of Glycosphingolipid Biosynthesis," *Cancer Lett.* 38:23–30 (1987), expressly incorporated by reference. The compounds of the present invention and in particular the aliphatic compounds require much lower doses than those previously described. This is particularly important because the lower dose may reduce certain side effects. Moreover, because the aliphatic compounds of the present invention do not produce ceramide accumulation, they are less toxic. In addition, 1-phenyl-2-palmitoylamino-3-pyrrolidino-1-propanol (P4), may act via two pathways, GSL depletion and ceramide accumulation.

In an alternative embodiment, a vaccine-like preparation is provided. Here, cancer cells are removed from the patient (preferably as completely as possible), and the cells are grown in culture in order to obtain a large number of the cancer cells. The cells are then exposed to the inhibitor for a time sufficient to deplete the cells of their GLSs (generally 1 to 5 days) and are reinjected into the patient. These reinjected cells act like antigens and are destroyed by the patient's immunodefense system. The remaining cancer cells (which could not be physically removed) will also be attacked by the patient's antibodies. In a preferred embodiment, the patient's circulating gangliosides in the plasma are removed by plasmapheresis, since the circulating gangliosides would tend to block the immunodefense system.

It is believed that tumors are particularly dependent on GSL synthesis for maintenance of their growth (Hakomori, S. "New Directions in Cancer Therapy Based on Aberrant Expression of Glycosphingolipids: Anti-adhesion and Ortho-Signaling Therapy," Cancer Cells 3:461–470 (1991)). Accumulation of ceramide in treated tumors also slows their growth or kills them. Tumors also generate large amounts of GSLs and secrete them into the patient's body, thereby preventing the host's normal response by immunoprotective cells, which should generate antibodies against or otherwise destroy tumor cells (e.g., tumors are weakly antigenic). It has also been shown that GSL depletion blocks the metastasis of tumor cells (Inokuchi, J. et al., "Inhibition of Experimental Metastasis of Murine Lewis Long Carcinoma by an Inhibitor of Glucosylceramide Synthase and its Possible Mechanism of Action," Cancer Res. 50:6731–6737 (1990). Tumor angiogenesis (e.g., the production of blood capillaries) is strongly influenced by GSLs (Ziche, M. et al., "Angiogenesis Can Be Stimulated or Repressed in In Vivo by a Change in GM3:GD3 Ganglioside Ratio," Lab. Invest. 67:711–715 (1992)). Depleting the tumor of its GSLs should block the tumors from generating the new blood vessels they need for growth.

A further important characteristic of the compounds of the present invention is their unique ability to block the growth of multidrug resistant ("MDR") tumor cells even at much lower dosages. This was demonstrated with PDMP by Rosenwald, A. G. et al., "Effects of the Glycosphingolipid Synthesis Inhibitor, PDMP, on Lysosomes in Cultured Cells," J. Lipid Res. 35:1232 (1994), expressly incorporated by reference. Tumor cells that survive an initial series of therapeutic treatments often reappear some years later with new properties—they are now resistant to a second treatment schedule, even with different drugs. This change has been attributed to the appearance in the tumor of large amounts of a specific MDR protein (P-glycoprotein). It has been suggested that protein kinase C (PKC) may be involved in the action or formation of P-glycoprotein (Blobe, G. C. et al., "Regulation of PKC and Its Role in Cancer Biology," Cancer Metastasis Rev. 13:411–431 (1994)). However decreases in PKC have other important effects, particularly slowing of growth. It is known that PDMP does lower the cellular content of PKC (Shayman, J. A. et al., "Modulation of Renal Epithelial Cell Growth by Glucosylceramide: Association with Protein Kinase C, Sphingosine, and Diacylglyceride," J. Biol. Chem. 266:22968–22974 (1991)) but it is not clear why it so effectively blocks growth of MDR cells (Rosenwald, A. G. et al., "Effects of the Glycosphingolipid Synthesis Inhibitor, PDMP, On Lysosomes in Cultured Cells," J. Lipid Res. 35:1232 (1994)). A recent report showed that several lipoidal amines that block MDR action also lower the level of the enzyme acid sphingomyelinase (Jaffrezou, J. et al., "Inhibition of Lysosomal Acid Sphingomyelinase by Agents which Reverse Multidrug Resistance," Biochim. Biophys. Acta 1266:1–8 (1995)). One of these agents was also found to increase the cellular content of sphingosine 5-fold, an effect seen with PDMP as well. One agent, chlorpromazine, behaves like the compounds of the present invention, in its ability to lower tissue levels of GlcCer (Hospattankar, A. V. et al., "Changes in Liver Lipids After Administration of 2-Decanoylamino-3-Morpholino-propiophenone and Chlorpromazine," Lipids 17:538–543 (1982)).

It will be appreciated by those skilled in the art that the compounds of the present invention can be employed in a wide variety of pharmaceutical forms; the compound can be employed neat or admixed with a pharmaceutically acceptable carrier or other excipients or additives. Generally speaking, the compound will be administered orally or intravenously. It will be appreciated that therapeutically acceptable salts of the compounds of the present invention may also be employed. The selection of dosage, rate/frequency and means of administration is well within the skill of the artisan and may be left to the judgment of the treating physician or attending veterinarian. The method of the present invention may be employed alone or in conjunction with other therapeutic regimens. It will also be appreciated that the compounds of the present invention are also useful as a research tool e.g., to further investigate GSL metabolism.

Compositions within the scope of invention include those comprising a compound of the present invention in an effective amount to achieve an intended purpose. Determination of an effective amount and intended purpose is within the skill of the art. Preferred dosages are dependent for example, on the severity of the disease and the individual patient's response to the treatment.

As used herein, the term "pharmaceutically acceptable salts" is intended to mean salts of the compounds of the present invention with pharmaceutically acceptable acids, e.g., inorganic acids such as sulfuric, hydrochloric, phosphoric, etc. or organic acids such as acetic.

Pharmaceutically acceptable compositions of the present invention may also include suitable carriers comprising excipients and auxiliaries which facilitate processing of the active compounds into preparations which may be used pharmaceutically. Such preparations can be administered orally (e.g., tablets, dragees and capsules), rectally (e.g., suppositories), as well as administration by injection.

The pharmaceutical preparations of the present invention are manufactured in a manner which is itself known, e.g., using the conventional mixing, granulating, dragee-making, dissolving or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets.

Suitable excipients are, in particular, fillers such as sugars, e.g., lactose or sucrose, mannitol or sorbitol, cellulose preparations and/or calcium phosphates, e.g., tricalcium diphosphate or calcium hydrogen phosphate, as well as binders such as starch paste, using, e.g., maize starch, wheat starch, rice starch, potato starch, gelatin, gum tragacanth, methyl cellulose and/or polyvinylpyrrolidone. If desired, disintegrating agents may be added such as the above-mentioned starches and also carboxymethyl starch, cross-linked polyvinylpyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvent or solvent mixtures. In order to produce coatings resistant to gastric juices, solutions of suitable cellulose preparations, such as acetylcellulose phthalate or hydroxypropylmethylcellulose phthalate, are used. Dyestuffs or pigments may be added to the tablets or dragee coatings, e.g., for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be used.

Possible pharmaceutical preparations which can be used rectally include, e.g., suppositories, which consist of a combination of the active compounds with a suppository base. Suitable suppository bases are, e.g., natural or synthetic triglycerides, paraffin hydrocarbons, polyethylene glycols or higher alkanols. It is also possible to use gelatin rectal capsules which consist of a combination of the active compounds with a base. Possible base materials include, e.g., liquid triglycerides, polyethylene glycols or paraffin hydrocarbons.

Suitable formulations for parenteral administration include aqueous solutions of the active compounds in water-soluble form, e.g., water-soluble salts. In addition, suspension of the active compounds as appropriate oily injection suspensions may be administered. Suitable lipophilic solvents or vehicles include fatty oils, such as sesame oil, or synthetic fatty acid esters, e.g., ethyl oleate or triglycerides. Aqueous injection suspensions may contain substances which increase the viscosity of the suspension such as sodium carboxymethylcellulose, sorbitol and/or dextran. Optionally, the suspension may also contain stabilizers.

Alternatively, the active compounds of the present invention may be administered in the form of liposomes, pharmaceutical compositions wherein the active compound is contained either dispersed or variously present in corpuscles consisting of aqueous concentrate layers adherent to hydrophobic lipidic layer. The active compound may be present both in the aqueous layer and in the lipidic layer or in the non-homogeneous system generally known as a lipophilic suspension.

The foregoing and other aspects of the invention may be better understood in connection with the following examples, which are presented for purposes of illustration and not by way of limitation.

SPECIFIC EXAMPLE 1

Synthesis of the Acetyl Derivative of D-t-3',4'-Ethylenedioxy-P4

A mixture of D-t-3',4'-ethylenedioxy-P4 (100 mg, 0.18 m mole), pyridine (0.3 ml) and acetic anhydride (1 ml) was stirred at RT for 2 days. All of the solvents were removed in vacuo. The residue was then purified by a silica column developed with 5% MeOH in CHCl$_3$.

SPECIFIC EXAMPLE 2

Synthesis of the Pyridinium Derivative of D-t-3',4'-Ethylenedioxy-P4

Nicotinic anhydride (0.07 m mole) was added to D-t-3',4'-ethylenedioxy-P4 (40 mg, 0.07 mmole DIEA (1 ml), CH$_2$Cl$_2$ (1 ml) and DMAP (3 mg) and stirred at RT for one day. The ester was purified by silica with 5% MeOH in chloroform.

DIEA: Diisopropylethylamine.
DMAP: 4-Dlmethyaminopyridine.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

All publications cited herein are expressly incorporated by reference.

What is claimed is:

1. A compound represented by the formula:

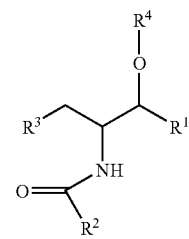

wherein
R$^1$ is an aromatic structure, an alicyclic structure, a branched aliphatic structure or a linear aliphatic group having 5 to 15 carbons;
R$^2$ is an aliphatic chain having 10 to 18 carbons;
R$^3$ is a cyclic tertiary amine; and
R$^4$ is an in vivo hydrolyzable group.

2. The compound of claim 1 wherein R$^3$ is pyrrolidino.

3. The compound of claim 1 wherein R$^1$ is 4-hydroxyphenyl.

4. The compound of claim 1 wherein R$^1$ is 3,4-ethylenedioxyphenyl.

5. A method for treating a patient having Gaucher's disease, Tay Sachs disease, Fabry's disease Sandhoff disease or GM1 gangliosidosis, comprising the step of administering to the patient a therapeutically effective amount of the compound of claim 1 or pharmaceutically acceptable salts thereof.

6. A compound selected from the group consisting of the formula:

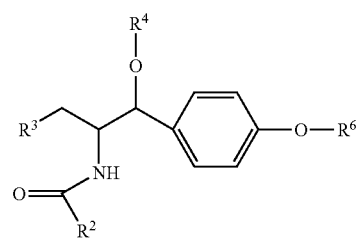

wherein
- $R^2$ is an aliphatic chain having 10 to 18 carbons;
- $R^3$ is a cyclic tertiary amine;
- $R^4$ is an in vivo hydrolyzable group or a hydrogen; and
- $R^6$ is an in vivo hydrolyzable group.

7. The compound of claim 6 wherein $R^3$ is pyrrolidino.

8. The compound of claim 6 wherein $R^1$ is 4-hydroxyphenyl.

9. The compound of claim 6 wherein $R^1$ is 3,4-ethylenedioxy.

10. A method for treating a patient having Gaucher's disease, Tay Sachs disease, Fabry's disease, Sandhoff disease or GM1 gangliosidosis, comprising the step of administering to the patient a therapeutically effective amount of the compound of claim 6 and pharmaceutically acceptable salts thereof.

11. A compound selected from the group consisting of the formulas:

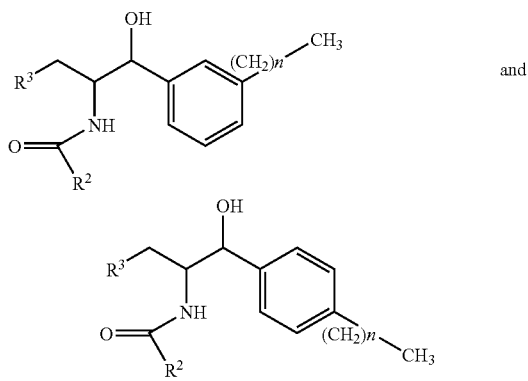

wherein
- n is an integer from about 1 to 19;
- $R_2$ is an aliphatic chain having 10 to 18 carbon atoms; and
- $R_3$ is a cyclic tertiary amine.

12. The compound of claim 11 wherein $R^3$ is pyrrolidino.

13. A method for treating a patient having Gaucher's disease, Tay Sachs disease, Fabry's disease, Sandhoff disease or GM1 gangliosidosis, comprising the step of administering to the patient a therapeutically effective amount of a compound selected from the group consisting of the formulas:

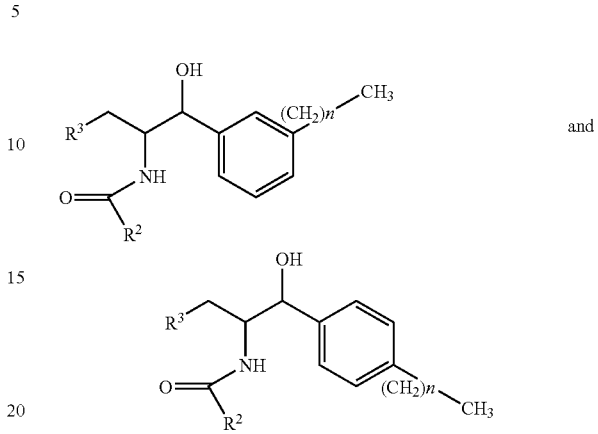

or pharmaceutically acceptable salts thereof.
- n is an integer from about 1 to 19;
- $R_2$ is an aliphatic chain having 10 to 18 carbon atoms; and
- $R_3$ is a cyclic tertiary amine.

14. The compound of claim 6 wherein hydrolyzable groups represented $R^4$ and $R^6$ are independently selected from the group consisting of an acetyl, —CO(CH$_2$)CH$_3$ and

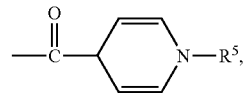

wherein $R^5$ is an alkyl group.

* * * * *

UNITED STATES PATENT AND TRADEMARK OFFICE
CERTIFICATE OF CORRECTION

PATENT NO. : 7,148,251 B2  Page 1 of 1
APPLICATION NO. : 10/044869
DATED : December 12, 2006
INVENTOR(S) : James A. Shayman It is certified that error appears in the above-identified patent and that said Letters Patent is hereby corrected as shown below:

Column 13, Line 38, please add --about-- between "to" and "19".

Column 14, Line 25, please add --about-- between "to" and "19".

Signed and Sealed this

Twenty-seventh Day of March, 2007

JON W. DUDAS
*Director of the United States Patent and Trademark Office*